(12) United States Patent
Coates

(10) Patent No.: US 9,220,828 B2
(45) Date of Patent: Dec. 29, 2015

(54) DIALYSIS MACHINE CONTROL

(75) Inventor: James Coates, Droitwich (GB)

(73) Assignee: QUANTA FLUID SOLUTIONS LTD, Alcester Warwickshire (GB)

( * ) Notice: Subject to any disclaimer, the term of this patent is extended or adjusted under 35 U.S.C. 154(b) by 1028 days.

(21) Appl. No.: 13/393,446

(22) PCT Filed: Jun. 15, 2010

(86) PCT No.: PCT/GB2010/001162
§ 371 (c)(1),
(2), (4) Date: Jul. 5, 2012

(87) PCT Pub. No.: WO2010/146344
PCT Pub. Date: Dec. 23, 2010

(65) Prior Publication Data
US 2012/0269907 A1    Oct. 25, 2012

(30) Foreign Application Priority Data

Jun. 15, 2009  (GB) .................... 0910244.3
Jun. 15, 2009  (GB) .................... 0910246.8
Jun. 15, 2009  (GB) .................... 0910247.6
Jul. 1, 2009   (GB) .................... 0911414.1

(51) Int. Cl.
*A61M 1/16*    (2006.01)
*B01F 15/04*   (2006.01)
*B01D 61/26*   (2006.01)
*B01D 61/28*   (2006.01)

(52) U.S. Cl.
CPC ......... *A61M 1/1656* (2013.01); *A61M 2205/12* (2013.01)

(58) Field of Classification Search
CPC .................. A61M 1/1656; A61M 2205/12
See application file for complete search history.

(56) References Cited

FOREIGN PATENT DOCUMENTS

| EP | 0623357 | 11/1994 |
|---|---|---|
| WO | WO2006120415 | 11/2006 |
| WO | WO2008106191 | 9/2008 |

*Primary Examiner* — John Kim
(74) *Attorney, Agent, or Firm* — Hahn Loeser & Parks, LLP

(57) ABSTRACT

A method of preparing a dialysate solution for hemodialysis, the method including the steps of providing a mixing pump comprising a pump chamber covered by an actuable membrane, the chamber having a first inlet for admitting water into the chamber, a second inlet for admitting dialysate base solution into the chamber, and an outlet from the chamber, the method including the further steps of providing pump means for dispensing a predetermined volume of dialysate solution base into the chamber at a first pressure, actuating the membrane to draw a volume of water or water mix into the mixing pump chamber at a second pressure, wherein the magnitude of the first pressure is higher than the magnitude of the second pressure so as to ensure the complete dispense of the dialysate solution base into the chamber.

9 Claims, 7 Drawing Sheets

FIG. 4

DIALYSIS MACHINE CONTROL

CROSS-REFERENCE TO RELATED APPLICATIONS

This application claims priority from PCT/GB/2010/001162 filed on Jun. 15, 2010, from GB 0910244.3 filed Jun. 15, 2009, from GB 0910246.8 filed Jun. 15, 2009, from GB 0910247.6 filed Jun. 15, 2009 and from GB 0911414.1 filed Jul. 1, 2009, all of which are hereby incorporated by reference in their entireties.

BACKGROUND OF THE INVENTION

1. Field of the Invention

The present invention relates to dialysis machines and in particular, but not exclusively, to a method of preparing a dialysate solution for use in dialysis.

2. State of the Art

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line, is treated by the dialysis machine, and is then returned to the body by a venous line. The machine passes the blood through a dialyser containing tubes formed from a semi permeable membrane. On the exterior of the semi permeable membrane is a dialysate solution. The semi permeable membrane filters the waste products and excess fluid from the blood into the dialysate solution. The membrane allows the waste and a controlled volume of fluid to permeate into the dialysate whilst preventing the loss of larger more desirable molecules, like blood cells and certain proteins and polypeptides.

The action of dialysis across the membrane is achieved primarily by a combination of diffusion (the migration of molecules by random motion from a region of higher concentration to a region of lower concentration), and convection (solute movement that results from bulk movement of solvent, usually in response to differences in hydrostatic pressure).

Fluid removal (otherwise known as ultrafiltration) is achieved by altering the hydrostatic pressure of the dialysate side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysis solution consists of a sterilized solution of mineral ions. These ions are contained within an acid buffer which is mixed with water and bicarbonate base prior to delivery to the dialyser. The water used is cleaned to a sufficient degree that it is suitable for use as a base for trans-membrane ion transfer with the blood (hereinafter sterile water), this may for example be achieved by known methods including reverse osmosis, heat treatment, filtration or a combination of such known methods.

Dialysate composition is critical to successful dialysis treatment since the level of dialytic exchange across the membrane, and thus the possibility to restore adequate body electrolytic concentrations and acid-base equilibrium, depends on the composition.

The correct composition is accomplished primarily by formulating a dialysate whose constituent concentrations are set to approximate normal values in the body.

However, achieving the correct composition of dialysate requires the accurate control of low volumes of liquid and at present this is achieved by the provision of complex fluid paths, including multiple pumping and valving components on the dialysis machine.

This presents the disadvantage of a complex and costly dialysis machine which is at increased risk of failure by virtue of its complexity. Increased maintenance is also a problem since it is essential to minimise machine downtime in order to most efficiently treat the patient.

A further problem with known hemodialysis machines is that the blood and dialysate solution lines require careful mounting onto the dialysis machine before the treatment can commence. This presents a risk that the lines are not correctly installed, a risk which is particularly relevant to those patients who dialyse at home.

This method of dialysis also presents an increased risk of cross-infection between patients since the disposable blood and dialysate lines come into contact with the dialysis machine.

The problems associated with conventional dialysis equipment are mitigated to some degree by the system disclosed in WO 2006/120415 which discloses a cartridge based system for conducting hemodialysis, however the method and system for mixing the dialysate proposed in this application is complex and costly involving a large cartridge with multiple reservoirs, each having level control and therefore requiring a complex pumping and control system. Both this complexity and this space requirement are undesirable in portable dialysis machines, for example those suitable for home dialysis.

SUMMARY OF THE INVENTION

It is an object of the present invention to provide a hemodialysis system which at least mitigates some of the problems described above.

According to the invention there is provided a method of preparing a dialysate solution for hemodialysis, the method including the steps of providing a mixing pump comprising a pump chamber covered by an actuable membrane, the chamber having a first inlet for admitting water into the chamber, a second inlet for admitting dialysate base solution into the chamber, and an outlet from the chamber, the method including the further steps of:

providing pump means for dispensing a predetermined volume of dialysate solution base into the chamber at a first pressure, actuating the membrane to draw a volume of water or water mix into the mixing pump chamber at a second pressure, wherein the magnitude of the first pressure is higher than the magnitude of the second pressure so as to ensure the complete dispense of the dialysate solution base into the mixing pump chamber.

According to a further aspect of the invention there is provided a method of preparing a dialysate solution for hemodialysis, the method including the steps of providing a mixing pump comprising a pump chamber covered by an actuable membrane, the chamber having a first inlet for admitting water or a water mix into the chamber, a second inlet for admitting dialysate base solution into the chamber, and an outlet from the chamber in fluid communication with a balance pump, providing pump means for dispensing dialysate solution base into the chamber via the second inlet, providing the water outlet, the base inlet and the pump outlet with respective valves to control flow there through, the method including the further steps of:

opening the second inlet valve, operating the pump means to dispense a predetermined volume of dialysate solution base into the chamber, closing the second inlet valve before the outlet valve is opened.

According to a further aspect of the invention there is provided a method of preparing a dialysate solution for hemodialysis, the method including the steps of providing a mixing pump comprising a pump chamber covered by an actuable membrane, the chamber having a first inlet for admitting water or a water mix into the chamber, a second inlet for admitting dialysate base solution into the chamber, and an outlet from the chamber in fluid communication with a balance pump chamber, the method including the further steps of:

providing pump means for dispensing a predetermined volume of dialysate solution base into the mixing pump chamber, wherein the volume of the mixing pump chamber is greater than the volume of the flow balance pump chamber.

Each of these aspects of the invention deliver the advantage that there is no need to provide a reservoir or other form of fluidic buffering between the acid and bicarbonate mixing pumps. The provision of predetermined volumes of acid and bicarbonate base solutions into the mixing pumps provide a self-regulating system that ensures that the constitution of the dialysate remains constant after a very brief start-up cycle. Each of the aspects provides a method of ensuring that the balancing pump is never starved of dialysate solution without the need for either the dumping of an oversupply of dialysate or closed loop control of the system.

The invention will now be described, by way of example only, and with reference to the following drawings.

DETAILED DESCRIPTION OF THE PREFERRED EMBODIMENTS

Figure 1:
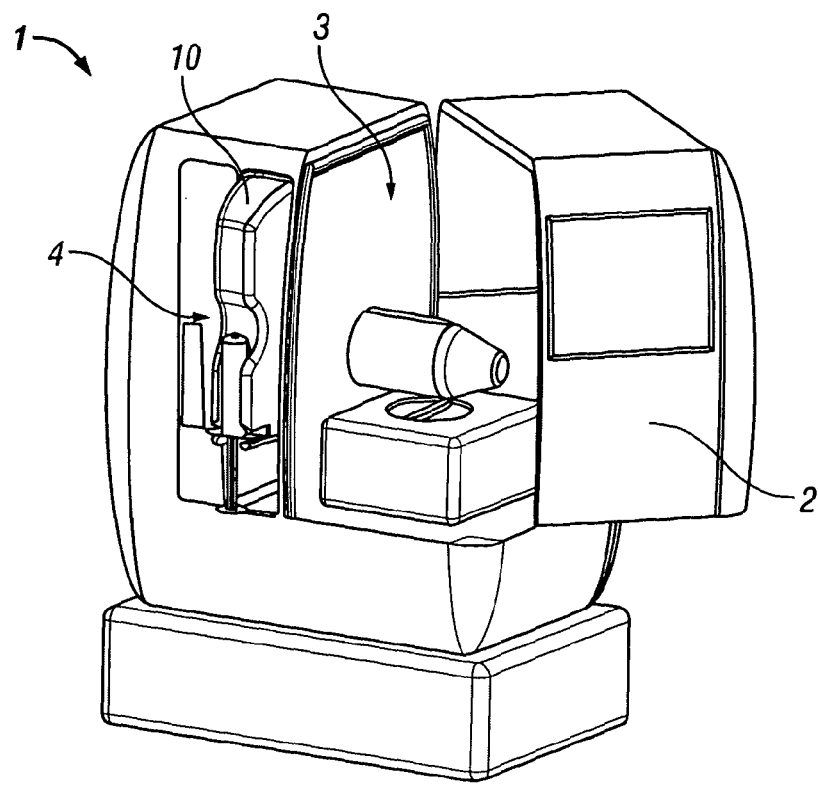
FIG. 1 is an isometric view of a dialysis machine.

In FIG. 1 a dialysis machine 1 is shown having a cover 2 which opens to reveal a storage compartment 3. The machine has an engine section 4 which receives a dialysis cartridge 10 which defines all of the fluid pathways required to perform a dialysis treatment.

Figure 2:
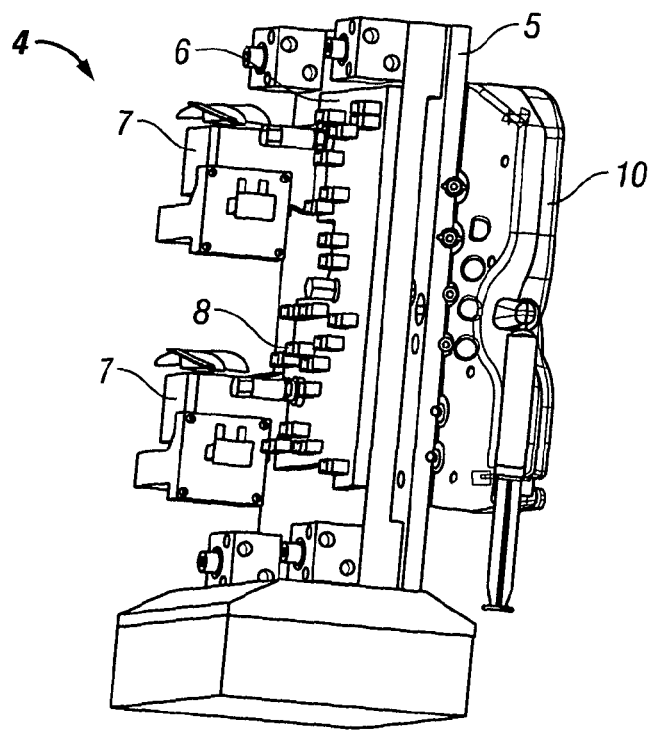
FIG. 2 is an isometric view of the fluid management portion of the machine of FIG. 1.

Referring now to FIG. 2, the engine section 4 is shown in further detail to include first and second platens 5, 6 which close upon insertion of the cartridge 10 into the machine to retain the cartridge in position in use. The engine 4 has pneumatic actuators 7 and sensors (indicated generally at 8 in FIG. 2) arranged on the second platen 6 to control operation of the cartridge 10 as will be described in further detail shortly.

Figure 3:
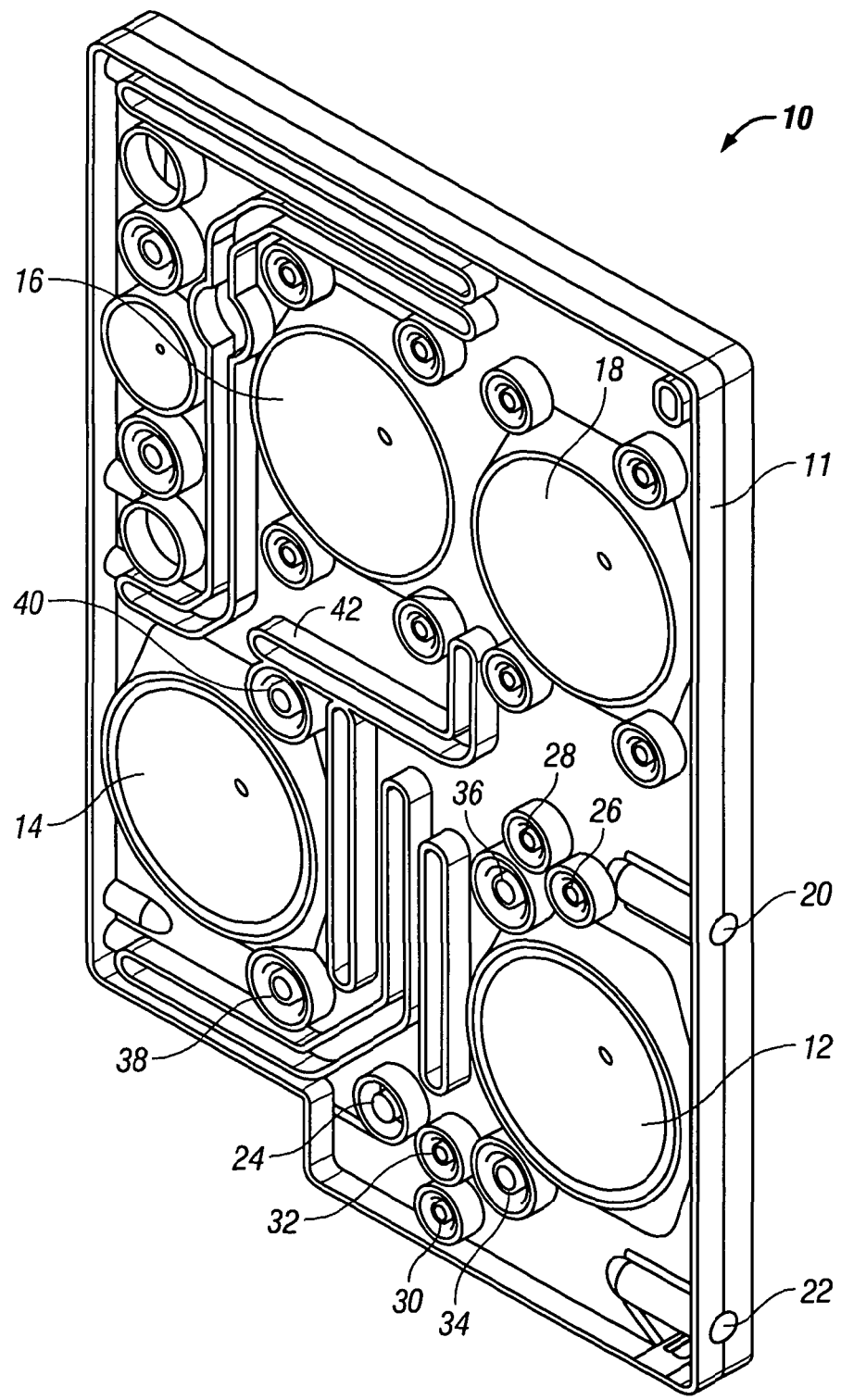
FIG. 3 is an isometric view of the cartridge of FIG. 1.

Referring to FIG. 3, the side of the cartridge which engages the second platen 6 is shown in greater detail. The purpose of the cartridge is to accurately mix the individual constituents of the dialysate solution, namely water (cleaned by reverse osmosis prior to arrival on the cartridge), bicarbonate base solution and acid base solution. Accordingly, the cartridge 10 has a moulded body 11 which defines a series of fluid flow channels and chambers which are covered by a flexible membrane which covers the cartridge and which is actuable by the pneumatic actuators on the second platen 6 as will be described in further detail shortly. The cartridge has a bicarbonate mixing pump 12, an acid mixing pump 14 and first and second flow balance pumps 16, 18 respectively. The cartridge further includes a syringe pump port 20, a bicarbonate syringe pump port 22, and a water inlet 24.

Associated with the acid syringe pump port 20 is an acid syringe pump inlet valve 26 and an acid syringe pump outlet valve 28. Similarly, associated with the bicarbonate syringe pump port 22 is a bicarbonate syringe pump inlet valve 30 and a bicarbonate syringe pump outlet valve 32. The acid syringe pump port 20 and bicarbonate syringe pump port 22 are provided to accommodate a syringe piston (not shown for clarity) controlled by a syringe driver (also not shown for clarity) on the machine 1 in order to dispense a predetermined volume of bicarbonate base solution and acid base solution into the bicarbonate mixing pump 12 and acid mixing pump 14, respectively, as will be described in further detail shortly.

The bicarbonate mixing pump 12 is provided with water inlet valve 34 and a bicarbonate mix output valve 36.

Associated with the acid mixing pump 14 is a mixing pump inlet valve 38 for admitting a bicarbonate mix and a dialysate outlet valve 40.

Accordingly, in use, reverse osmosis water is cleaned prior to admission onto the cartridge via the reverse osmosis inlet valve 24. A pre-determined volume of bicarbonate base solution is dispensed into the pump 12 by a bicarbonate syringe pump 41 (not show in FIG. 3 for clarity). Water is drawn into the bicarbonate mixing pump 12 by the application of a negative pressure by the engine 4 to the outer surface of the membrane. The water and bicarbonate base solution are thoroughly mixed in the pump 12 by the action of the membrane pumping the fluid. This is achieved by the engine 4 applying a positive pressure to the membrane. In this way the mixed solution is pumped through the bicarbonate mix output valve 36 into the acid pump 14 via the inlet valve 38. A predetermined volume of acid base solution is administered by the acid base solution pump 43 (not shown in FIG. 3 for clarity) into the acid pump 14 where it is thoroughly mixed with the bicarbonate-water mix by the action of the membrane being actuated to pump the dialysate from the acid pump 14 via the pump chamber outlet 40. From the pump chamber outlet 40 the dialysate passes up channel 42 in order to be pumped by the first flow balance pump 16. From the first flow balance pump 16 the dialysate passes through the dialyser (not shown in FIG. 3 for clarity) before returning to the second flow balance pump 18 where it is pumped to drain (not shown for clarity).

Each of the valves are of a known design whereby the application of a positive pressure on the membrane by the engine 4 in the region of the valve closes the valve and the relief of the positive pressure opens the valve.

The detailed control of the mixing of the bicarbonate base solution with the reverse osmosis water in the bicarbonate pump 12 will now be discussed in further detail with reference to FIG. 4.

Figure 4:
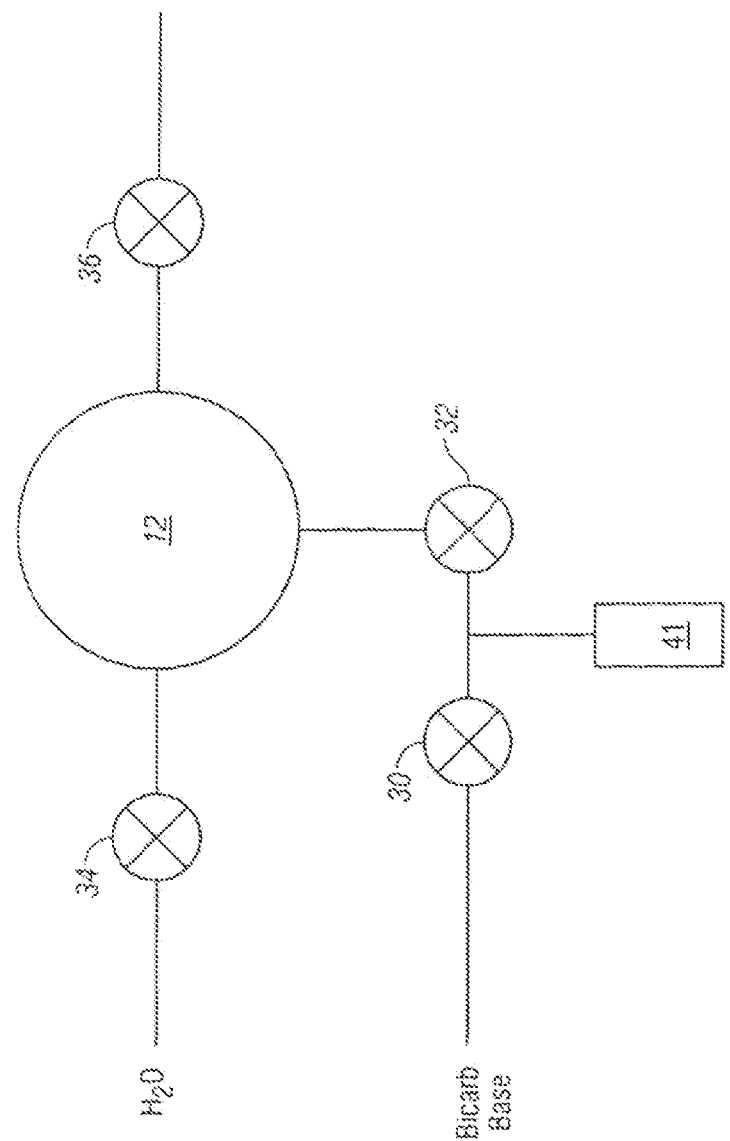
FIG. 4 is a schematic representation of the bicarbonate mixing pump of the cartridge of FIG. 3.

FIG. 4 shows a schematic layout of the bicarbonate pump 12, the water inlet valve 34, the bicarbonate inlet valve 30 and outlet valve 32 and the bicarbonate mix output valve 36.

The bicarbonate base solution syringe pump is shown schematically at 41. The syringe pump 41 is provided by way of an actuable syringe positioned within the bicarbonate base syringe port 22. In use, the bicarbonate base solution inlet valve 30 is opened to allow the syringe pump 41 to draw into the bicarbonate base syringe port 22 a predetermined volume of bicarbonate base from a supply to the machine 1. The inlet valve 30 is then closed, and the outlet valve 32 opened allowing the depression of the syringe within the bicarbonate base syringe port 22 to deliver the predetermined volume of bicarbonate base solution into the mixing pump 12. The volume of bicarbonate base solution administered is determined by the patient's clinical requirements and is absolutely critical to the effectiveness of the dialysis treatment. At the same time as, or shortly after, the syringe bicarbonate base solution outlet valve 32 is opened, the reverse osmosis water inlet valve 34 is also opened. Negative pressure is applied to the outside surface of the membrane 11 in order to draw water through the water inlet valve 34 and into the mixing pump 12. Once the membrane has been actuated to its full stroke, the water inlet valve 34 is closed, and the bicarbonate mix output valve 36 is opened allowing the actuation of the membrane to pump the mixture out of the pump 12. If the water inlet valve 30 is opened at the same time as the bicarbonate base is administered into the pump 12 by the bicarbonate base solution syringe pump 41 then the syringe pump must be operated at a higher pressure than the mixing pump 12 in order to ensure that the full predetermined volume of bicarbonate base is dispensed.

Figure 5:
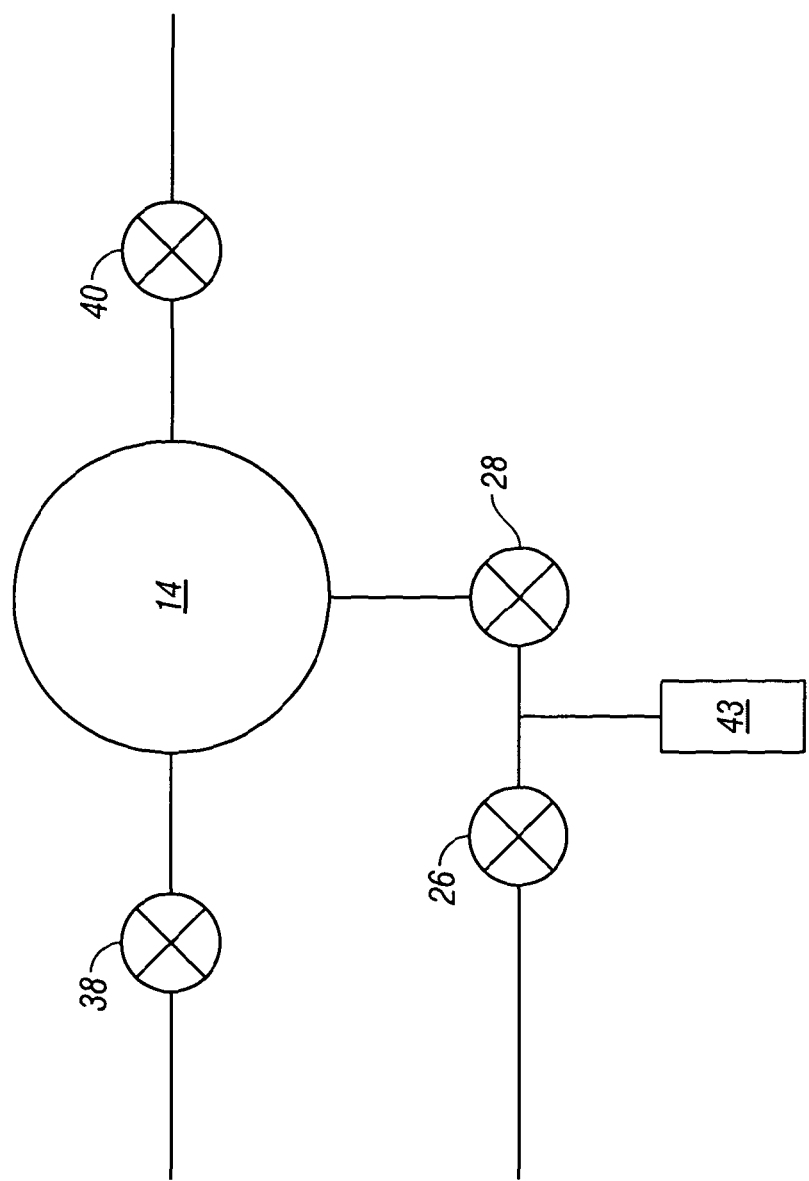
FIG. 5 is a schematic representation of the acid mixing pump of the cartridge of FIG. 3.

FIG. 5 shows a schematic layout of the acid pump chamber 14, the inlet valve 38, the acid syringe pump inlet valve 26, acid syringe pump outlet valve 28 and dialysate mix outlet valve 40.

The acid base solution syringe pump is showing schematically at 43. The syringe pump 43 is provided by way of an actuable syringe positioned within the acid base syringe port 20. In use, the acid base solution inlet valve 26 is opened to allow the syringe pump 43 to draw into the acid base syringe port 20 a predetermined volume of acid base solution from a supply to the machine 1. The inlet valve 26 is then closed, and the outlet valve 28 is opened allowing the depression of the syringe within the acid base syringe port 20 to deliver the predetermined volume of acid base solution into the mixing pump 14. Like the bicarbonate base solution, the volume of acid base solution administered is determined by the patient's clinical requirements in a known manner and is absolutely critical to the effectiveness of the dialysis treatment. At the same time as, or shortly after, the outlet valve 28 is opened, the acid mixing pump inlet valve 38 is also opened. Negative pressure is applied to the outside surface of the membrane 11 in order to draw the bicarbonate-water mix through the inlet valve 38 and into the mixing pump 14. Once the membrane has been actuated to its full stroke, the inlet valve 38 is closed, and the dialysate mix outlet valve 40 is opened allowing the actuation of the membrane to pump the mixture out of the pump 14. If the inlet valve 38 is opened at the same time as the acid base is administered into the pump 12 by the acid base solution syringe pump 43 then the syringe pump must be operated at a higher pressure than the mixing pump 12 in order to ensure that the full predetermined volume of acid base is dispensed.

Figure 6:
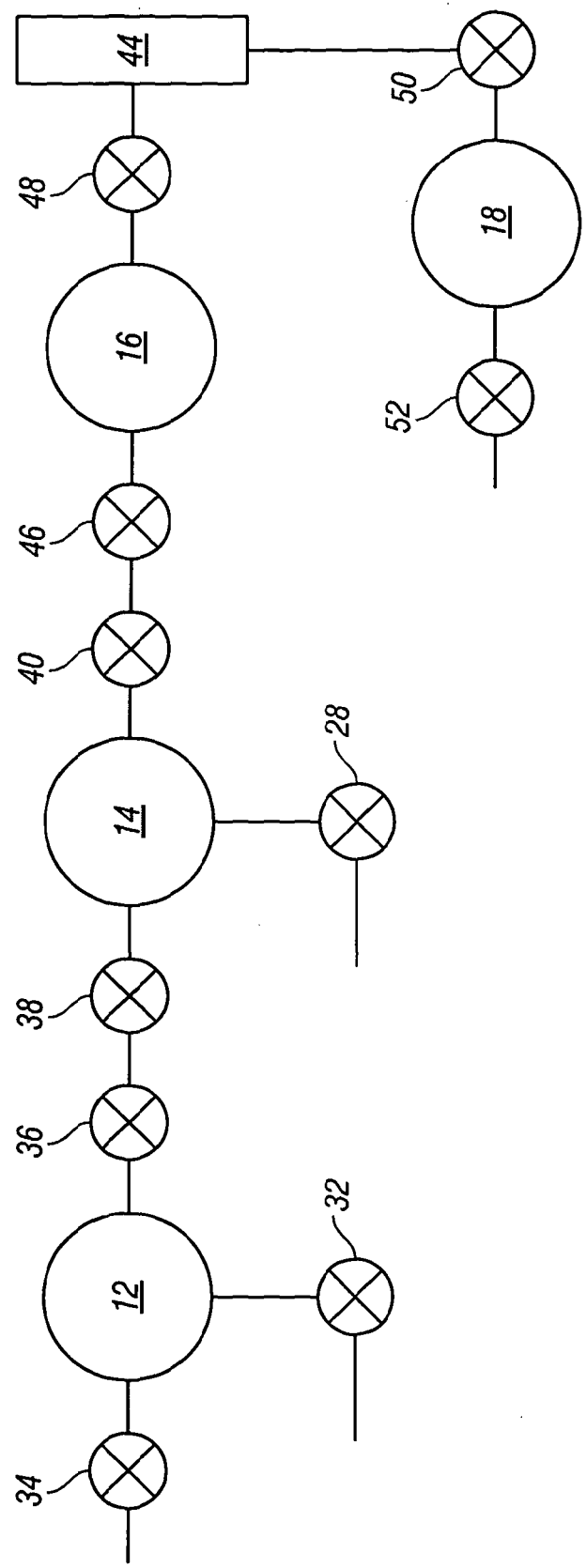
FIG. 6 is a schematic representation of the acid mixing pump, bicarbonate mixing pump and flow balance pumps of the cartridge of FIG. 3, and a dialyser.

Referring now to FIG. 6, the bicarbonate pump and associated valves as shown in FIG. 4, and the acid pump 14 and associated valves as shown in FIG. 5 are brought together schematically with the first and second flow balance pumps 16, 18. Also shown schematically is a dialyser which houses the trans-membrane interface between the dialysate and the blood to be dialysed. First flow balance pump inlet and outlet valves 46, 48 are shown on either side of the first flow balance pump 16, and similarly second flow balance pump inlet and outlet valves 50, 52 are shown on either side of the second flow balance pump 18 in order to control flow of dialysate across the dialyser in a known manner.

In use the fully mixed dialysate solution exits the acid dialysate mix outlet valve 40 and passes through the first flow balance pump inlet valve 46 to be pumped by the first flow balance pump 16 to the dialyser 44 via the first flow balance pump outlet valve 48. The used dialysate solution exits the dialyser and passes through the second flow balance pump inlet valve 50 before being pumped by the second flow balance pump 18 to drain via the second flow balance pump outlet valve 52.

Figure 7:
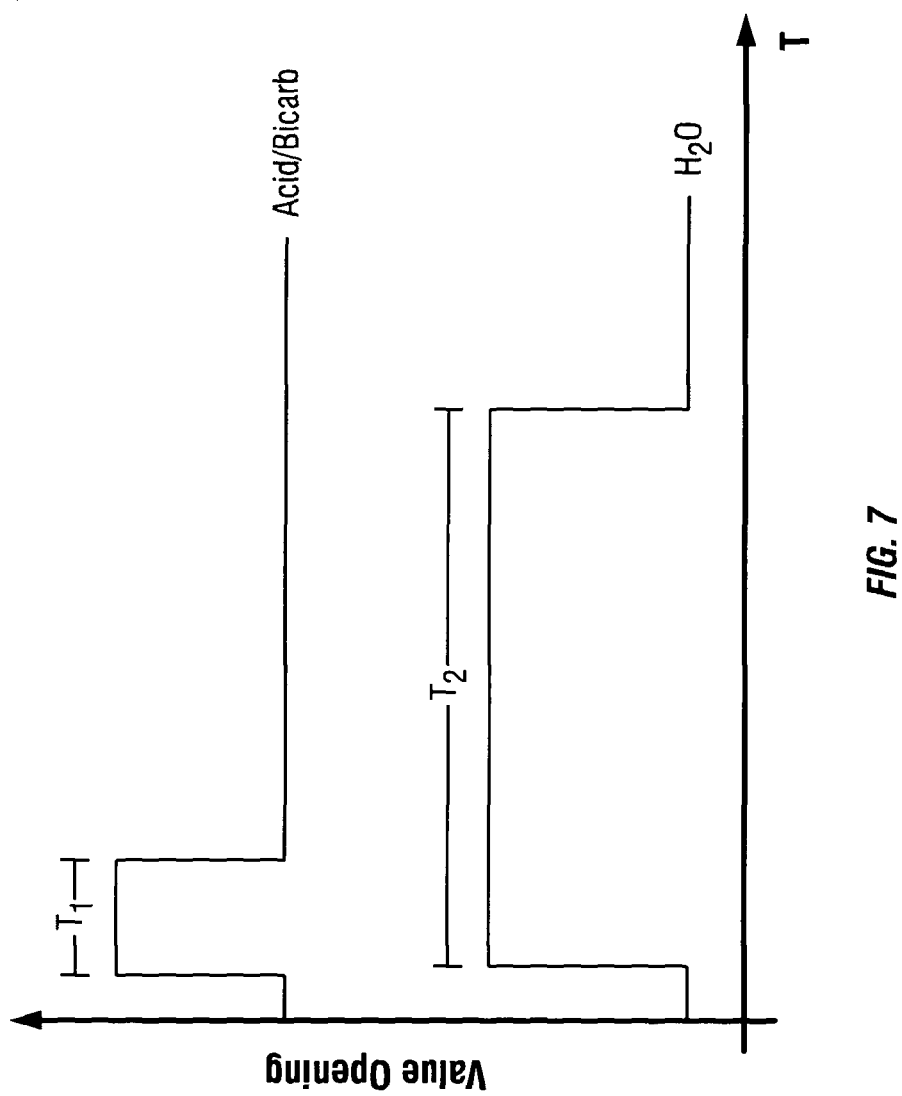
FIG. 7 is a plot showing the timing of the opening of the water inlet valves.

Turning now to FIG. 7, the chart shows two plots, the lower plot depicting the opening time $T_2$ of the inlet valves 34, 38 to the bicarbonate and acid pump chambers 12, 14 respectively, the upper plot shows the opening time $T_1$ of the dialysate base solution inlet valves 32, 28 of the bicarbonate and acid mixing pumps 12, 14 respectively. As shown in the chart, the time of opening of the acid and bicarbonate base solution valves 32, 28 is less than the opening times of the inlet valves 34, 38. This ensures that the predetermined volume of either acid or bicarbonate base solution is admitted into the respective mixing pump before the pump chamber achieves full volume. This can be achieved either by operating the inlet valves in sequence or by operating the base solution syringe pumps 41, 43 at a higher pressure than the mixing pumps 12, 14, or a combination of both methods.

This in turn ensures that over the course of a single treatment, the correct volumetric ratio of acid and bicarbonate base solutions to the overall volume of the first flow balance pump 16 is achieved.

The volume of each of the bicarbonate pump chamber 12 and acid pump chamber 14 is greater than the volume of the first flow balance chamber 16. Since the total volume of dialysate passing through the dialyser is determined by the volume of flow balance chamber 16, it follows that the predetermined volume of acid and bicarbonate base solution introduced into the bicarbonate pump chamber 12 and acid pump chamber 14 is set to the volume of the flow balance chamber 16. However, since the bicarbonate pump chamber 12 and acid pump chamber 14 are larger than the flow balance chamber, the concentration of the bicarbonate solution in the bicarbonate pump chamber 12 on the first stroke of the pump will be reduced by the inverse of the relative sizes of the bicarbonate pump chamber 12 and flow balance pump chamber 16.

For example if the flow balance pump chamber 16 is 10% smaller than the bicarbonate pump chamber 12 and acid pump chamber 14, then the concentration of the solution in the bicarbonate pump chamber 12 on the first stroke of the bicarbonate mixing pump will be (100−10)=90% of the required concentration. On the second stroke, 10% of the volume will be at 90% concentration and the remaining 90% will be 100% so the overall mixture will be at 99% of the required concentration. On the third stroke, 10% of the volume will be at 99% of the concentration and the remaining 90% will be at 100% so the overall mixture will be at 99.9%. Accordingly the concentration converges on 100% of the required accuracy without the need for reservoirs or active control.

The same convergence occurs if the concentration of the solution is changed in the middle of treatment.

Figure 8:
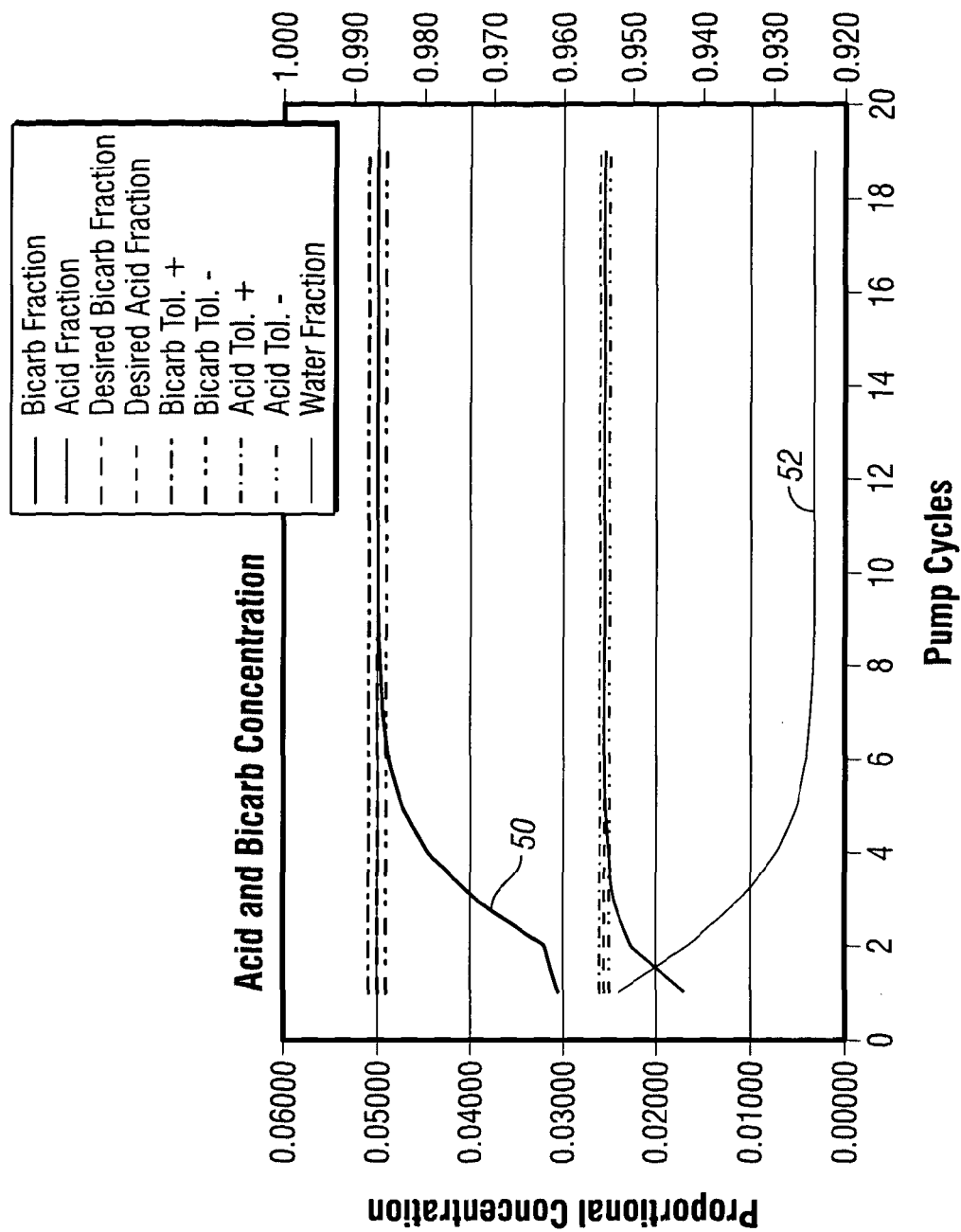
FIG. 8 is a plot showing the proportional concentration of the acid and swab in the mixed dialysate.

This principle is demonstrated in FIG. 8 which shows the stabilising of the acid concentration 50 and the bicarbonate concentration 52 within 8 to 10 pump cycles. Thus, after a short settling in time, the present invention delivers accurately mixed dialysate to the flow balance pump without the need for fluidic buffering or closed loop control of the dispensed volumes of acid and bicarbonate.

It will be appreciated within the scope of the invention that whilst the pump means for administering acid and bicarbonate base solutions are described as syringe pumps, they could equally be membrane pumps with a similar mode of operation to the mixing pumps.

The invention claimed is:

1. A method of pr paring dialysate solution for hemodialysis, the method comprising:
providing a first mixing pump comprising a pump chamber covered by an actuable membrane, the chamber having a first inlet the admitting water or a water mix into the chamber, a second inlet the admitting dialysate base solution into the chamber, and an outlet from the chamber;
using pump means to dispense a predetermined volume of dialysate base solution into the chamber at a first pressure; and
actuating the membrane to draw a volume of water or water mix into the mixing pump chamber at a second pressure;
wherein a magnitude of the first pressure is higher than a magnitude of the second pressure, and wherein the predetermined volume of dialysate base solution is dispensed into the chamber before completion of operation of the first mixing pump to draw the volume of water or water mix into the chamber, so as to ensure complete dispense of the dialysate base solution into the chamber.

2. The method of claim 1, wherein:
the volume of water is drawn into the chamber after the predetermined volume of dialysate base solution is administered into the chamber.

3. The method of claim 1, further comprising:
providing the first inlet, second inlet and outlet with a valve to control flow there through.

4. The method of claim 1, wherein:
the pump means for dispensing the dialysate base solution is a positive displacement pump or membrane pump.

5. The method of claim 1, further comprising:
providing a second mixing pump, wherein the dialysate base solution dispensed into the first mixing pump is a bicarbonate concentrate and a dialysate base solution dispense. into the second mixing pump is an acid concentrate, and wherein the outlet from the first mixing pump carries a water/bicarbonate mix to a first inlet of the second mixing pump;
providing a pre-determined volume of the acid concentrate to the second mixing pump;
operating the first and second mixing pumps sequentially to deliver the dialysate from an outlet of the second mixing pump.

6. A method of preparing a dialysate solution for hemodialysis, the method comprising;
providing a first mixing pump comprising a pump chamber covered by an actuable membrane, the chamber having a first inlet for admitting water or a water mix into the chamber, a second inlet for admitting dialysate base solution into the chamber, and an outlet from the chamber;
providing first pump means for dispensing dialysate base solution into the chamber via the second inlet;
providing the first inlet, the second inlet and the pump outlet with respective valves to control flow there through;
opening the second inlet valve, and operating the first pump means to dispense a predetermined volume of dialysate base solution into the chamber;
operating the first mixing pump to draw a volume of water or water mix into the pump chamber, wherein the drawing in the volume of water or water mix is started after the dispensing the dialysate base solution is completed; and
closing the second inlet valve before the outlet valve is opened.

7. The method of claim 6, further comprising:
providing a second mixing pump, wherein the dialysate base solution dispensed into the first mixing pump is a bicarbonate concentrate and a dialysate base solution dispensed into the second mixing pump is an acid concentrate, and wherein the outlet from the first mixing pump carries a water/bicarbonate mix to a first inlet of the second mixing pump;
providing a second pump means for dispensing the acid concentrate into a second inlet of the second mixing pump;
providing the first inlet, the second inlet and an outlet of the second mixing pump with respective valves to control flow there through;
opening the second inlet valve of the second mixing pump, and operating the second pump means to dispense a predetermined volume of the acid concentrate Into the second mixing pump;
operating the second mixing pump to draw it volume of the water/bicarbonate mix into the second mixing pump, wherein the drawing in the volume of water/bicarbonate mix is started after the dispensing the acid concentrate is completed;
closing the second inlet valve of the second mixing pump before the outlet valve of the second mixing pump is opened; and
operating the first and second mixing pumps sequentially to deliver the dialysate from the outlet of the second mixing pump.

8. A method of preparing a dialysate solution for hemodialysis, the method comprising:
providing a mixing pump comprising a mixing pump chamber covered by an actuable membrane, the mixing pump chamber having a first inlet for admitting water or a water mix into the chamber, a second inlet for admitting dialysate base solution into the mixing pump chamber, and an outlet from the mixing pump chamber in fluid communication with a balance pump chamber; and
using pump means to dispense a predetermined volume of dialysate base solution into the mixing pump chamber at a first pressure, wherein a volume of the mixing pump chamber is greater than a volume of the balance pump chamber.

9. The method of claim 8, further comprising:
determining the predetermined volume of dialysate base solution based on a clinically required concentration of dialysate and the volume of the balance pump chamber.

* * * * *

UNITED STATES PATENT AND TRADEMARK OFFICE
CERTIFICATE OF CORRECTION

| | | |
|---|---|---|
| PATENT NO. | : 9,220,828 B2 | Page 1 of 1 |
| APPLICATION NO. | : 13/393446 | |
| DATED | : December 29, 2015 | |
| INVENTOR(S) | : James Coates | |

It is certified that error appears in the above-identified patent and that said Letters Patent is hereby corrected as shown below:

in column 7, line 23, (first line of claim 1), delete "pr paring" and substitute therefor --preparing--.

in column 7, line 27, (fifth line of claim 1), delete "inlet the admitting" and substitute therefor --inlet for admitting--.

in column 7, line 28, (sixth line of claim 1), delete "inlet the admitting" and substitute therefor --inlet for admitting--.

in column 7, line 55, (fifth line of claim 5), delete "dispense." and substitute therefor --dispensed--.

in column 8, line 35, (seventeenth line of claim 7), delete "Into" and substitute therefor --into--.

in column 8, line 37, (nineteenth line of claim 7), delete "draw it volume" and substitute therefor --draw a volume--.

Signed and Sealed this
Twenty-eighth Day of June, 2016

Michelle K. Lee
*Director of the United States Patent and Trademark Office*